United States Patent [19]

Riedel et al.

[11] Patent Number: 4,589,874
[45] Date of Patent: May 20, 1986

[54] EXTERNAL MALE CATHETER AND APPLICATOR COLLAR THEREFOR

[75] Inventors: Kenneth E. Riedel, Naperville; David L. Doerschner, Rolling Meadows, both of Ill.

[73] Assignee: Hollister Incorporated, Libertyville, Ill.

[21] Appl. No.: 714,716

[22] Filed: Mar. 21, 1985

[51] Int. Cl.⁴ .................................. A61F 5/44
[52] U.S. Cl. ........................... 604/349; 206/229
[58] Field of Search ........... 604/349, 317, 323, 335; 206/229

[56] References Cited

U.S. PATENT DOCUMENTS

| 4,187,851 | 2/1980 | Hauser | 128/295 |
| 4,270,231 | 6/1981 | Zint | 604/349 |
| 4,378,018 | 3/1983 | Alexander et al. | 128/295 |
| 4,475,910 | 10/1984 | Conway et al. | 604/352 |
| 4,484,918 | 11/1984 | Omley | 604/349 |
| 4,540,409 | 9/1985 | Nystrom et al. | 604/349 |

Primary Examiner—Arthur P. Demers
Attorney, Agent, or Firm—Tilton, Fallon, Lungmus

[57] ABSTRACT

An external male urinary drainage catheter combined with a collar for facilitating proper fitting of the catheter upon a patient, and the method of using such a catheter/collar combination, are disclosed. The catheter includes a cylindrical section rolled to form a torus that is supported by the collar prior to catheter application, a tapered neck section that extends through the open-ended collar, and an inner sleeve portion that is held in a stretched condition by the collar to help insure placement of the sleeve in sealing engagement with the glans of a patient's penis during the initial stage of catheter application.

13 Claims, 8 Drawing Figures

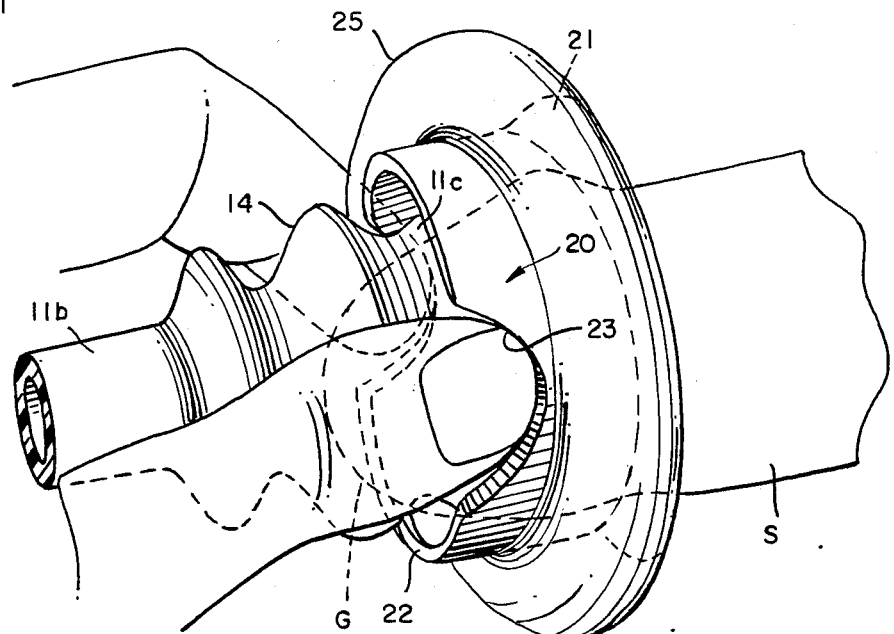
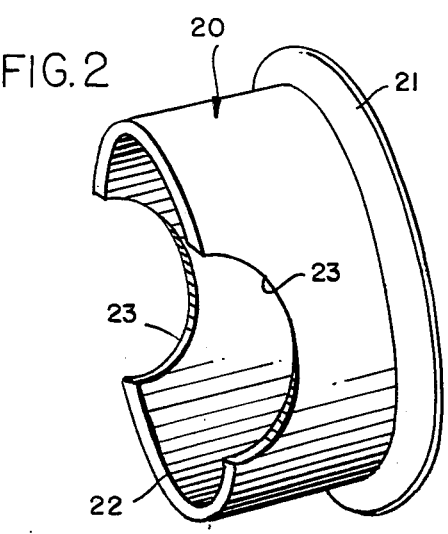
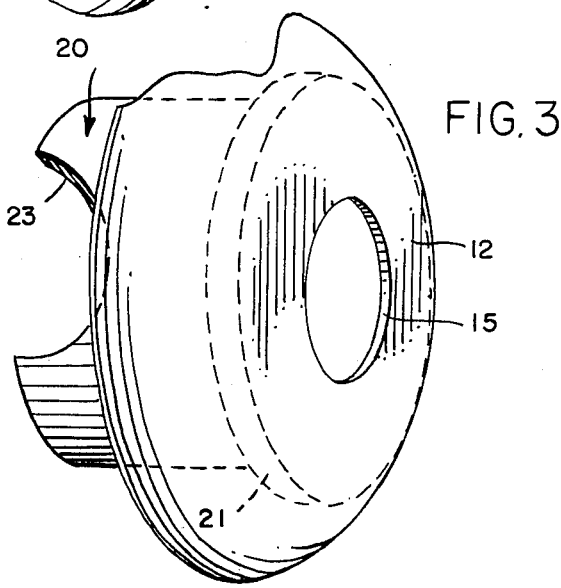
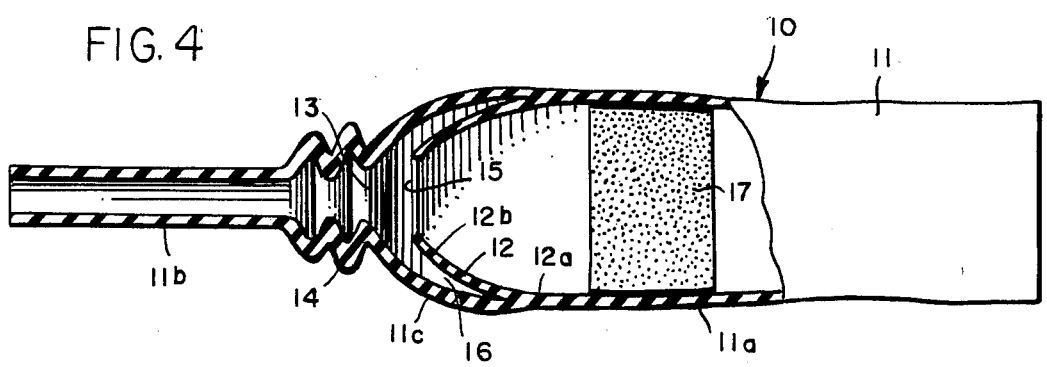

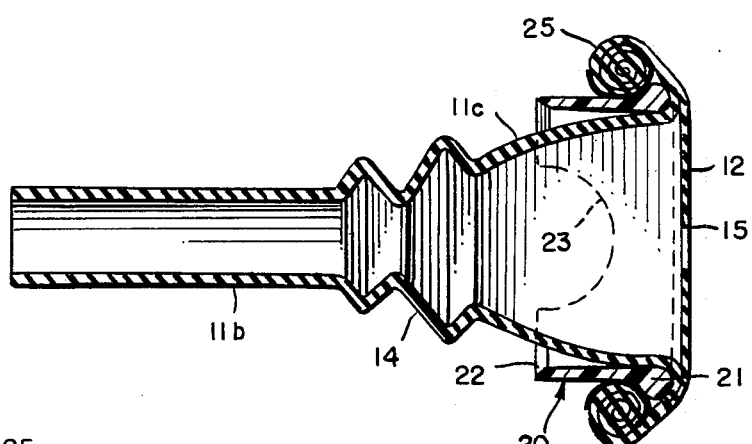
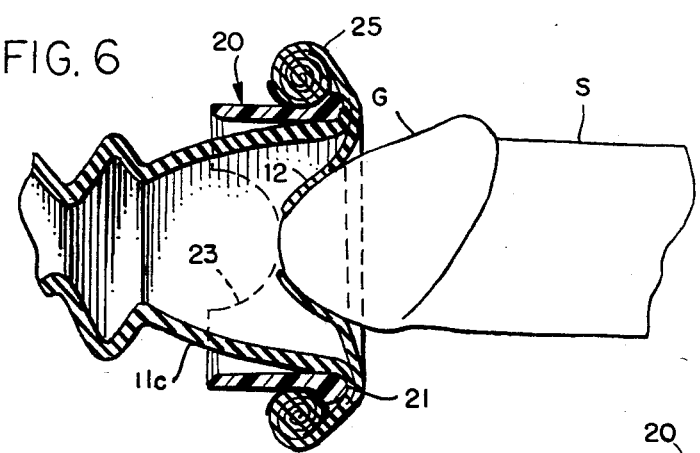
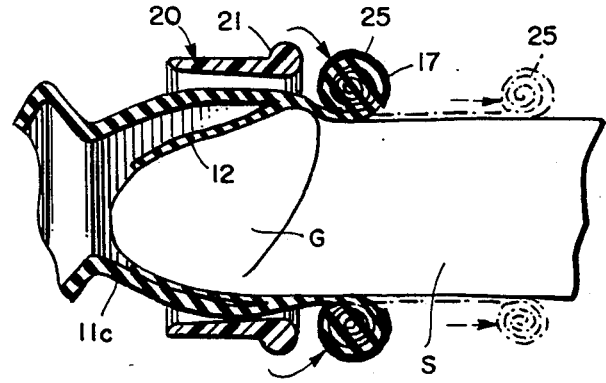
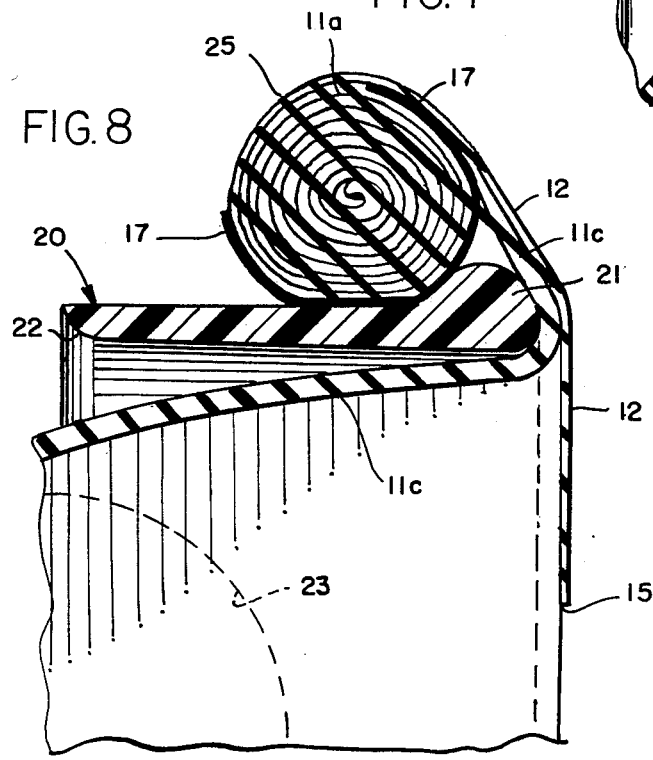

EXTERNAL MALE CATHETER AND APPLICATOR COLLAR THEREFOR

BACKGROUND

The use of external catheters for male urinary drainage systems is well known, as disclosed in U.S. Pat. Nos. 4,378,018, 4,187,851, 3,863,638, 3,835,857 and 4,475,910. Essentially, such a system comprises an elastic sheath adapted to fit over the user's penis, the sheath having an outlet at its distal end connected to a tube leading to a suitable collection receptacle. Since leakage resulting from fluid backflow between the penis and sheath is clearly undesirable, it has become a common practice to interpose a sealant pad between the sheath and the penile shaft as disclosed, for example, in U.S. Pat. No. 4,187,851 and in co-owned U.S. Pat. No. 4,378,018.

While a sealant pad, when properly used, performs the dual functions of preventing leakage and retaining the catheter in place, difficulties have been reported in fitting such pads and catheters upon users exactly as intended. For example, a pad of the type depicted in U.S. Pat. No. 4,187,851 takes the form of an adhesive strip intended to be wrapped about the penile shaft before the elastic catheter is unrolled into position over the penis. Performing such operations may be difficult or impossible by patients suffering from urinary incontinence since such patients often lack the motor control and/or mental acuity necessary for such manipulations. Nurses or other attendants may be unable to take the time necessary for properly wrapping and molding the sealant pads in place, and for then carefully fitting the sheaths over the pads to form leakproof seals. Should errors be made that might increase the possibilities of subsequent leakage, a nurse or attendant might nevertheless leave the improperly-applied pad and catheter in place because of time constraints or because of patient discomfort that might be associated with removing the improperly-applied pads and starting over. Moreover, problems resulting from improper application of an appliance might be more serious than occasional fluid leakage or mild patient discomfort. Thus, should an adhesive pad of the type shown in U.S. Pat. No. 4,187,851 be wrapped too tightly about the penile shaft, circulation might be impaired and tissue necrosis could result.

External catheters are currently available that are internally coated with pressure-sensitive adhesive and therefore eliminate the need for using separate adhesive-coated sealant pads, as shown, for example, in U.S. Pat. No. 4,475,910. While such a construction avoids some of the more serious dangers associated with wrap-around sealant pads, the difficulties of application, and the problems of leakage resulting from improper application, persist and may even be more pronounced. Considerable care must be taken when unrolling an adhesive-coated sheath over the penis to make certain that the sheath is evenly applied without developing wrinkles and flow channels. All too frequently the adhesive-coated inner surfaces of such a sheath come into contact with each other during application of the catheter. Separation of the contacting surfaces, if possible at all, is difficult and time-consuming, with the result that corrective steps may not be taken and leakage of the catheter in later use is practically assured.

Co-pending co-owned application Ser. No. 613,279, filed May 24, 1984, discloses an external male catheter having an inner sleeve designed to be stretched about the glans of the penis to prevent backflow and protect the delicate skin of the glans from injury caused by long-term contact with residual urine that may remain near the outlet end of the sheath when the catheter is used, especially by a patient confined to bed. A similar catheter with an inner sleeve is also disclosed in co-owned co-pending application Ser. No. 510,904, filed July 5, 1983. Such a catheter, whether held in place by adhesive coating or an adhesive pad, requires for proper operation that the inner sleeve be stretched into fluid-tight sealing contact with the glans before the proximal cylindrical portion of the catheter is adhesively secured to the penile shaft.

Other prior patents of general interest are Swedish Pat. No. 162302 and U.S. Pat. Nos. 4,022,213, 4,284,079, 3,405,714, 4,239,044, 3,353,538, 3,511,241, 3,721,243, 3,631,857, 3,788,324, 3,339,551, 3,364,932, 4,296,502, and 3,742,953.

SUMMARY OF THE INVENTION

This invention is directed to a catheter/applicator combination in which the external catheter is intended to be adhesively retained on the penis, preferably by a coating of pressure-sensitive adhesive applied to the inner surface of the catheter during its manufacture, and has an integral inner sleeve designed to be stretched over and sealingly engage the glans of the penis to protect the skin of the glans and provide an expandable space between the inner sleeve and the outer sheath to accommodate surges of fluid and prevent fluid backflow that might, if it were not for the inner sleeve, disrupt the adhesive connection between the catheter and the penile shaft. The applicator coacts with the catheter to facilitate proper orientation of the inner sleeve in relation to the glans at the time the catheter is fitted in place. Further aspects of the invention relate to the method for applying a catheter having an inner sleeve with the aid of an applicator that eliminates or greatly reduces the possibility that the catheter may accidentally be fitted improperly upon the patient.

The external catheter used in this combination takes the form of a sheath of thin, stretchable elastic material having a generally cylindrical section merging at one end with a tapered neck section terminating in an outlet section of reduced diameter, and an inner sleeve having a proximal end merging with the distal end of the cylindrical section and an elongated tapered distal portion extending into the neck section and terminating in a distal opening spaced from the outlet section. Such a catheter is depicted and described in the aforementioned co-pending application Ser. No. 613,279, filed May 24, 1984.

The applicator takes the form of a relatively rigid open-ended collar formed of polyethylene or other suitable plastic material. The collar is provided at one end with an external annular bead. At or near its opposite end, the collar is provided with a pair of diametrically-disposed recesses that are large enough to accommodate a user's fingers when the catheter is being fitted upon a patient. When the parts are combined, the catheter has its cylindrical section rolled to form a torus that extends about and is supported by the collar with the bead of the collar serving as retaining means. The neck and outlet sections of the catheter extend forwardly through the opening of the collar, and the inner sleeve extends from the torus over the collar's bead and then radially inwardly at the collar's proximal end. The radially inwardly extending portion of the inner sleeve is supported in stretched and generally planar condition along a plane normal to the central axis of the collar.

The torus, formed of the rolled cylindrical section of the catheter, has an inner diameter smaller than the outside diameter of the bead; therefore, the bead retains the torus on the collar until an axial unrolling force is exerted on the torus of a magnitude sufficient to stretch or expand the torus outwardly and permit it to unroll over the bead.

In use, the catheter/applicator combination is gripped by the fingers of one hand to direct the catheter's stretched inner sleeve against the glans of the penis. As the collar is advanced to receive the glans, the stretched sleeve portion wraps about the glans, conforming to its contour and sealingly engaging its surfaces. With the sleeve sealingly engaging the glans, the user simultaneously holds the collar and neck portion of the catheter stationary relative to the glans (such operation being greatly facilitated by the diametrically-disposed finger-receiving recesses formed in the collar) and then, using the fingers of the other hand, unrolls the torus over the bead of the collar and along the penile shaft.

Other features, advantages, and objects of the invention will become apparent from the specification and drawings.

DRAWINGS

FIG. 1 is a perspective view showing a catheter and applicator combination as it is about to be used in fitting the external catheter upon a male organ.

FIG. 2 is a perspective view showing only the applicator.

FIG. 3 is a fragmentary perspective view showing the applicator and collar combination as it would appear from its proximal end.

FIG. 4 is an elevational view, shown partly in section, of a catheter of the type used in the combination of this invention.

FIG. 5 is a sectional view showing the catheter and applicator combination as it would be supplied to a user.

FIG. 6 is a sectional view similar to FIG. 5 but showing a first step in the application of the catheter to a patient.

FIG. 7 is similar to FIG. 6 but illustrates subsequent steps in the application of the catheter.

FIG. 8 is an enlarged detailed view of a portion of FIG. 5.

DETAILED DESCRIPTION OF PREFERRED EMBODIMENT

The external male urinary drainage catheter which constitutes one element of the two-element combination of this invention incorporates the features disclosed in co-owned co-pending application Ser. No. 613,279, filed May 24, 1984. Such an external catheter 10 is shown most clearly in unrolled condition in FIG. 4. It is formed of soft, highly elastic, natural or synthetic rubber. Natural latex is preferred but other elastomers having similar properties may be used. The catheter includes an elongated outer sheath 11 and an inner sleeve 12, the two being integral or permanently integrated as hereinafter described.

Outer sheath 11 includes an elongated cylindrical section 11a, a reduced drainage tube section 11b, and a tapered neck section 11c disposed therebetween. The wall thickness of the cylindrical section 11a is substantially less than that of the neck and drainage tube sections. For example, the cylindrical section may have a wall thickness within the general range of 0.006 to 0.010 inches and, in general, is too thin or limp to retain a cylindrical configuration without support. In contrast, the wall thicknesses of the drainage tube and neck sections might be 0.050 inches or more and are generally great enough so that such sections will retain the configurations shown in the absence of distorting forces and will spring back into the illustrated shapes when distorting forces are removed.

At its forward or distal end, neck section 11c is provided with a rounded taper leading to a reduced opening 13. In addition, the neck section is provided with a plurality of convolutions or annular enlargements 14. Two such convolutions of graduated size are depicted, their purpose being to permit greater stretchability, bending, and twisting of the drainage tube and neck sections when the device is in use, and to do so with less chance that kinking or obstruction of the lumen might occur. Also, such convolutions increase the fluid capacity at the distal end of the neck section and provide a reservoir for accommodating surges of fluid when the device is in use.

Inner sleeve 12 has a proximal end portion 12a that merges smoothly with the distal end of the sheath's cylindrical body section 11a and an elongated distal end portion 12b disposed within the sheath's neck section 11c. The distal end portion 12b tapers forwardly and inwardly, terminating in a reduced distal opening 15 that is spaced well behind (i.e., proximal to) opening 13. The setback also results in the provision of an annular and axially-elongated expansion space 16 between the outer surface of the sleeve's distal end portion 12b and the inner surface of neck section 11c. The wall thickness of the sleeve may be varied but, to insure conformability, good sealing properties, and wearer comfort, such thickness should approximate that of the relatively thin cylindrical body section 11a. Thus, both the cylindrical body section 11a and the inner sleeve 12b should appear as thin, limp, highly stretchable membranes, in contrast to the drainage tube and neck sections 11b and 11c with their shape-retaining properties.

The adhesive means for adhesively securing the catheter to the penile shaft may take the form of a separate adhesive pad that is pre-applied before the catheter is fitted upon a wearer or, alternatively, as an adhesive coating along the inside surface of the catheter's cylindrical section 11a. Both are fully disclosed in the aforementioned co-pending application Ser. No. 613,279, although only the latter version is depicted here in FIG. 4. Adhesive zone 17 is located within the cylindrical section 11a of the sheath behind inner sleeve 12. While the adhesive coating might conceivably extend the full length of the cylindrical section 11a, it is believed preferable to provide the adhesive zone in the form of a narrow but continuous band located within the distal portion of the sheath's cylindrical section 11a. The adhesive coating may be composed of any suitable medical-grade pressure-sensitive adhesive of a type well known in the art; a hypo-allergenic acrylic adhesive is believed to be particularly effective.

The applicator takes the form of a short tube or collar 20 as shown most clearly in FIGS. 2 and 5–8. The short open-ended collar 20 is generally cylindrical in configuration although, as shown in the drawings, the preferred embodiment has a slight taper. The collar may be composed of any of a wide variety of relatively stiff or rigid plastic materials. A polyolefin such as high density polyethylene is believed particularly suitable, but other polymeric materials having similar properties would also be appropriate. Non-polymeric materials might also be used as, for example, cardboard.

The collar is provided with a smoothly-rounded external enlargement or bead 21 at its proximal end. At its opposite or distal end, the inner surface is beveled or radiused as shown at 22. A pair of enlarged recesses are formed in the cylindrical wall of the collar, such recesses being diametrically disposed and preferably of arcuate configuration. More specifically, when the collar is viewed in elevation, each recess has a generally semicircular shape opening at the distal end of the collar. Each recess has an axial dimension approximately half the length of the collar, and the length of the collar itself is less than the collar's diameter and substantially less than the length of the neck section 11c of the catheter.

The catheter and collar are supplied to a user with the catheter mounted upon the collar as shown in FIGS. 1, 3, 5, and 8. The cylinrical section 11a of the catheter is rolled upon itself to form a torus 25. Collar 20 is dimensioned so that its outer diameter, exclusive of bead 21, is approximately the same, or only slightly greater, than the inside diameter of torus 25. Bead 21 therefore has an outside diameter significantly larger than the inside diameter of the torus, with the result that the bead serves as retention means to hold the torus in place until a sufficient axial unrolling force is exerted on the torus to cause it to stretch or expand outwardly to clear the bead.

The neck section 11c extends from torus 25 inwardly about bead 21 and then forwardly or distally through the opening of collar 20. The convoluted portion 14 is fully exposed beyond the collar's distal end, as is outlet section 11b of the catheter.

Of particular importance is the fact that the inner sleeve 12 is supported in stretched or tensioned condition at the proximal end of collar 20. The sleeve extends from the torus 25 about bead 21 and then radially inwardly along a plane normal to the axis of the collar (FIGS. 3, 5, 8). Except for its central opening 15, the inner sleeve therefore appears as a membrane stretched across the proximal end of the collar. Bead 21 therefore performs the dual functions of preventing torus 25 from unrolling and, by reason of such restraint, maintaining the inner sleeve in the stretched and generally planar condition shown.

It will be noted from FIG. 8 that the adhesive layer or zone 17 is located far enough from the merger of the inner sleeve 12 and neck section 11c that the outermost surfaces of the torus are free of adhesive coating. Thus, there is no risk that the adhesive 17 might adhere to the inner surfaces of an envelope or package (not shown) in which the assembly will be marketed and stored. Although the cylindrical section of the catheter is coiled into torus shape, the adhesive does not adhere to the outer surface (when unrolled) of the cylindrical section 11a because of a release coating or layer of silicone rubber or other suitable release material, or because of a removal release strip or layer, all as well known in the art for the purposes of preventing unintended adherence between pressure-sensitive adhesives and adjacent surfaces.

FIGS. 1 and 6–7 illustrate the method of applying the external catheter to a patient. The user first grips the exposed distal portion of the collar and directs the stretched membrane-like inner sleeve 12 into contact with the glans (FIG. 6). Because the inner sleeve is in stretched condition, it may be applied evenly and uniformly to the glans. Once the glans is fully received within the opening of collar 20 and sleeve portion 12 is fully stretched over the glans in firm sealing contact with it, the user grips the neck section 11c and holds it firmly against the glans as shown most clearly in FIG. 1. Such operation is greatly facilitated by the enlarged recesses 23 which serve as finger openings for gripping the catheter's neck section 11c and the glans G, and for also immobilizing or holding the collar as, with the fingers of the other hand, the user urges torus 25 rearwardly over bead 21 (FIG. 7). As the torus unrolls, the adhesive layer 17 is brought into contact with the shaft S of the penis behind the corona of the glans, such adhesive contact thereby securing the external catheter in operative position with the inner sleeve 12 stretched over the glans as shown in FIG. 7. The torus is unrolled the length of the penile shaft, as indicated by broken lines in FIG. 7, collar 20 is removed and discarded, and the outlet section 11b of the catheter is connected to a suitable drainage tube (not shown).

While in the foregoing we have disclosed an embodiment of the invention in considerable detail for purposes of illustration, it will be understood by those skilled in the art that many of these details may be varied without departing from the spirit and scope of the invention.

We claim:

1. An external catheter and applicator combination, said catheter comprising a sheath of thin, stretchable, elastic material having a generally cylindrical section merging in one end with a tapered neck section terminating in an outlet section of reduced diameter, and an inner sleeve having a proximal end merging with the distal end of said cylindrical section and an elongated tapered distal portion extending into said neck section and terminating in a distal opening spaced from said outlet section; said applicator comprising a relatively rigid and generally cylindrical collar having open proximal and distal ends and an external annular bead with smoothly rounded surfaces at its proximal end; said catheter having its neck section extending through said collar, its outlet section projecting axially from the distal end of said collar, its cylindrical section rolled into a torus extending about said collar adjacent said bead, and its inner sleeve extending from said torus over said bead and radially inwardly at the proximal end of said collar; the radially inwardly extending portion of said inner sleeve being in stretched condition and generally disposed in a plane normal to the axis of said collar; said torus in an unstretched state having an inner diameter smaller than the outside diameter of said bead, whereby, said bead retains said torus on said collar until an unrolling force is exerted on said torus of sufficient magnitude to expand the inside diameter thereof.

2. The combination of claim 1 in which said collar has a length less than that of said neck portion of said catheter.

3. The combination of claim 2 in which said collar has an axial length substantially greater than the axial length of said torus.

4. The combination of claims 1, 2, or 3 in which said collar is provided with a pair of diametrically-disposed recesses adjacent the distal end thereof in which a user's fingers may be received for immobilizing said neck portion of said catheter and said collar relative to the glans of a penis as said torus is unrolled over said head and along the penile shaft.

5. The combination of claim 4 in which each of said recesses is arcuate.

6. The combination of claim 5 in which each of said recesses has an axial length approximately one half the length of said collar.

7. The combination of claim 1 in which said collar has a diameter greater than the length thereof.

8. The combination of claim 1 in which said collar is formed of a polyolefin.

9. The combination of claim 8 in which said polyolefin is high density polyethylene.

10. The combination of claim 1 in which said cylindrical section of said catheter has an annular layer of pressure-sensitive adhesive along at least a portion of its length; said layer of adhesive being disposed on that side of said cylindrical portion that contacts the penile shaft when the catheter is worn.

11. A method of applying an external male catheter to the penis of a patient, said catheter including a sheath of thin, stretchable, elastic material having a generally cylindrical section merging at one end with a tapered neck section terminating in an outlet section of reduced diameter, and an inner sleeve having a proximal end merging with the distal end of said cylindrical section and an elongated tapered distal portion extending into said neck section and terminating in a distal opening spaced from said outlet section; said catheter being supported by a generally cylindrical and relatively rigid collar having open proximal and distal ends and an external bead at said proximal end; said catheter being supported with said neck section extending through said collar, said outlet section projecting axially from the collar's distal end, said cylindrical section rolled into a torus about said collar adjacent said bead, and said inner sleeve extending from said torus over said bead with the portion thereof adjacent said sleeve opening extending radially inwardly in stretched condition along a plane normal to the axis of said collar; said method comprising the steps
gripping said collar and catheter between the fingers and urging said stretched sleeve portion against the glans of a patient's penis; advancing said collar and catheter to position said collar around the glans and to cause said stretched sleeve portion to wrap about said glans; then holding said collar and neck portion of said catheter stationary relative to said glans while unrolling said torus over said bead and along the penile shaft.

12. The method of claim 11 in which there is the further step of removing said collar from around said glans.

13. The method of claim 11 in which said collar is provided with a pair of diametrically-disposed recesses adjacent the distal end thereof, and wherein said step of holding said collar and neck portion stationary relative to said glans comprises inserting opposing fingers of one hand through said recesses and into contact with said neck section of said catheter to hold said neck section against the glans while at the same time immobilizing said collar against axial and rotational movement relative to said glans.

* * * * *